US010369396B1

(12) United States Patent
Edwards et al.

(10) Patent No.: US 10,369,396 B1
(45) Date of Patent: Aug. 6, 2019

(54) ASSEMBLY FOR DECONTAMINATING AND METHOD OF MANUFACTURING THE ASSEMBLY

(71) Applicant: Battelle Memorial Institute, Columbus, OH (US)

(72) Inventors: Erik W. Edwards, Gahanna, OH (US); Steven Risser, Reynoldsburg, OH (US); Jeffrey Boyce, Grove City, OH (US)

(73) Assignee: Battelle Memorial Institute, Columbus, OH (US)

( * ) Notice: Subject to any disclaimer, the term of this patent is extended or adjusted under 35 U.S.C. 154(b) by 0 days.

(21) Appl. No.: 16/186,059

(22) Filed: Nov. 9, 2018

(51) Int. Cl.
*A62D 3/30* (2007.01)
*B65D 81/32* (2006.01)
*A62D 101/26* (2007.01)
*A62D 101/02* (2007.01)

(52) U.S. Cl.
CPC ........... *A62D 3/30* (2013.01); *B65D 81/3266* (2013.01); *A62D 2101/02* (2013.01); *A62D 2101/26* (2013.01)

(58) Field of Classification Search
CPC .............................. A62D 3/30; B65D 81/3266
USPC ........................................................ 588/313
See application file for complete search history.

(56) References Cited

U.S. PATENT DOCUMENTS

| | | |
|---|---|---|
| 5,071,887 A | 12/1991 | Bannard et al. |
| 5,075,297 A | 12/1991 | Bannard et al. |
| 5,077,316 A | 12/1991 | Bannard et al. |
| 5,364,617 A | 11/1994 | Bush et al. |
| 6,525,237 B1 | 2/2003 | Purdon et al. |
| 7,214,836 B2 | 5/2007 | Brown et al. |
| 7,662,759 B1 | 2/2010 | Tucker et al. |
| 8,022,265 B2 | 9/2011 | Tucker |
| 8,084,622 B2 | 12/2011 | Vempati et al. |
| 8,518,941 B2 | 8/2013 | Kaiser et al. |
| 9,308,234 B2 | 4/2016 | Arnold et al. |
| 9,334,098 B1 | 5/2016 | Hughes |
| 9,604,085 B2 | 3/2017 | Henry et al. |
| 9,700,644 B2 | 7/2017 | Kaiser et al. |
| 2015/0157887 A1 | 6/2015 | Chilcott |
| 2017/0151198 A1 | 1/2017 | Mangino |
| 2018/0271770 A1 | 9/2018 | Henry et al. |

FOREIGN PATENT DOCUMENTS

DE 10010373 2/2002

OTHER PUBLICATIONS

Bogan et al. "Chemical stability of reactive skin decontamination lotion (RSDL®)." *Toxicology letters* 293 (2018): 264-268.
Elsinghorst et al. "Detoxification of organophosphorus pesticides and nevre agents through RSDL: efficacy evaluation by 31P NMR spectroscopy." *Toxicology letters* 233, No. 2 (2015): 207-213.
Kim et al. "Destruction and Detection of Chemical Warfare Agents." *Chemical Reviews* 111 (2011): 5345-5403.
Koplovitz et al. *Evaluation of Verioz as a Skin Decontamination Product after Dermal Exposure to the Nerve Agent CX.* No. USAMRICD-TR-16-06. US Army Medical Research Institute of Chemical Defense Aberdeen Proving Ground United States, 2016.
Salerno et al. "In Vitro skin decontamination of the organophosphorus pesticide Paraoxon with nanometric cerium oxide $CeO_2$." *Chemico-Biological Interactions* 267 (2017): 57-66.
Smith et al. "Efficacy and Design of Low-Cost Personal Decontamination System (LPDS) Formulations for Sulfur Mustard and Assorted TICs." *Lawrence Livermore National Laboratory* (2005).
Taysse et al. "Skin decontamination of mustards and organophosphates: comparative efficiency of RSDL and Fuller's earth in domestic swine." *Human & exoerimental toxicology* 26, No. 2 (2007): 135-141.

*Primary Examiner* — Edward M Johnson
(74) *Attorney, Agent, or Firm* — Diederiks & Whitelaw, PLC

(57) ABSTRACT

An assembly containing a shelf-stable formulation for decontaminating skin exposed to toxic compounds located in a package formed with water and potassium bicarbonate in a first chamber; and a sponge, diacetylmonoxime (DAM), and polyethylene glycol (PEG) located in a second chamber. The package includes a barrier between the first chamber and the second chamber, with the barrier being configured to be rapidly removed when needed to enable the water and potassium bicarbonate to enter the second chamber. The package is made by placing the water and potassium bicarbonate in the first chamber of a package; mixing the DAM with PEG to form a DAM:PEG mixture; infusing the sponge with the DAM:PEG mixture to distribute DAM within the sponge; and placing the sponge, DAM and PEG in a second chamber of the package. Infusing the sponge includes solubilizing the DAM:PEG mixture in ethanol or another low boiling point solvent to form an ethanol-DAM-PEG solution and applying the ethanol-DAM-PEG solution evenly to the sponge. The ethanol is removed by applying heat and/or vacuum to the sponge.

20 Claims, 18 Drawing Sheets

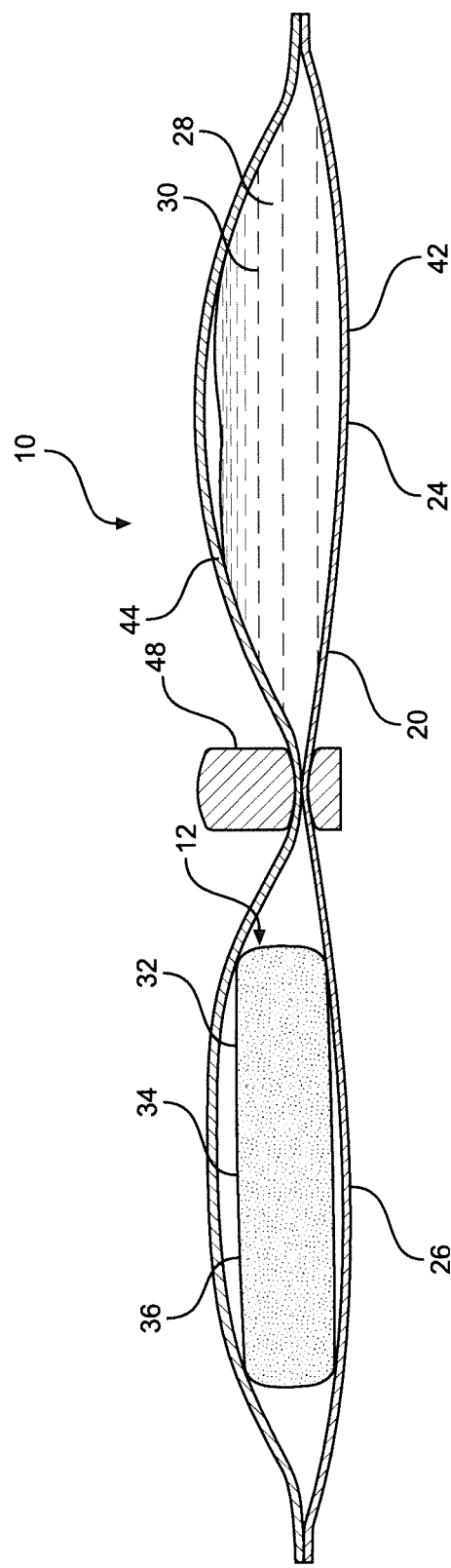
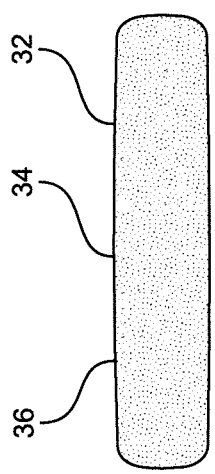
FIG. 1B
FIG. 1C

ASSEMBLY FOR DECONTAMINATING AND METHOD OF MANUFACTURING THE ASSEMBLY

TECHNICAL FIELD

The present invention relates to improving the shelf life and storage stability of key components of a formulation for treating skin that has been exposed to toxic compounds.

BACKGROUND

Various types of chemical weapons have been developed. Most of these chemical weapons are effective when their active ingredients come in contact with skin. Military personnel are most likely to require a defense against such weapons. In response, the United States Department of Defense (DoD) has developed numerous ways to counter chemical weapons, including detectors, specialized clothing and products designed to decontaminate skin exposed to such weapons. Unfortunately, with the threat of terrorism increasing, first responders are also in need of protection against chemical weapons. Chemical weapon attacks are not frequent such that any products designed to decontaminate skin must be stored for relatively long periods of time between potential attacks. In addition, there are certain agrichemicals such as pesticides that work in a similar manner to the active ingredients in chemical weapons such that there is also a need to protect or treat workers in industrial settings.

One product used to decontaminate skin is Reactive Skin Decontaminating Lotion (RSDL) which is a skin decontaminating lotion used by the DoD to treat people who have been exposed to toxic compounds such as chemical or nerve agents. RSDL contains diacetylmonoxime (DAM) which can complex with potassium bicarbonate to form potassium 2, 3-butanedione monoxime (KBDO). Both DAM and KBDO can serve as active ingredients for skin decontamination, along with polyethylene glycol monomethyl ether (MPEG) and water as a solvent/emollient system. RSDL is primarily effective against organophosphoruous (OP) nerve agents. Military personnel are issued pouches, each containing a sponge that is soaked with RSDL. When skin is exposed to a suspected organophosphoruous compound, RSDL is applied by tearing open the pouch, removing the sponge and scrubbing the exposed skin with the saturated sponge. The RSDL is left on the skin to allow the active ingredients to react with the OP nerve agents and penetrate into the skin tissue. The RSDL is ultimately removed by washing.

Skin exposed to organophosphoruous compounds must be treated immediately. Therefore, military personnel must store and carry RSDL so that the RSDL is readily available. RSDL is water sensitive. DAM is postulated to degrade into dimethylglyoxime (DMG) in the presence of water via hydrolysis and oximation mechanisms. See FIG. 1 of the non-patent literature to Bogan et al. ("Chemical stability of reactive skin decontamination lotion (RSDL®)"), which is incorporated herein by reference. Currently, RSDL will degrade over time and has a shelf life at 30° C. of only four years. Furthermore, if the RSDL is kept outside of that temperature range for even a short period of time, the material will be substantially degraded. Therefore, there exists a need for a treatment of exposure to OP compounds and nerve agents that has a long shelf life (i.e. greater than 5 years at 50° C.) but which can also be readily applied to exposed skin when needed. Specifically, DoD personnel in the field and civil first responders need decontamination product formulations and packaging that have enhanced shelf lives and performances over time compared to current decontamination products.

SUMMARY

The present invention relates to an assembly containing a shelf-stable formulation, for decontaminating skin exposed to toxic compounds such as nerve agents, located in a package formed with a first chamber and a second chamber. Water is located in the first chamber and potassium bicarbonate may be added to the water; and a sponge, polyethylene glycol (PEG), and diacetylmonoxime (DAM) are located in the second chamber. The DAM and PEG are distributed within the sponge. Preferably, the package is formed of a transparent or metallized flexible packaging material. The package further comprises a barrier between the first chamber and second chamber, which is configured to be rapidly removed, when needed, to enable the water (and optionally potassium bicarbonate) to enter the second chamber. The package is also configured to be easily opened so one can remove the sponge after the sponge has been exposed to the water and potassium bicarbonate and use the sponge to apply the DAM to exposed skin. The package is made of plastic or metallized plastic and the barrier is either a mechanical clamp or a thermoformed seal. Preferably, a ratio of potassium bicarbonate to water, by weight, is less than 1 to 3.6 and the ratio of DAM to PEG, by weight, is approximately 2.25. The resulting package has a projected shelf life of, at least 6 years at 50° C. and can withstand short-term thermal excursions of up to 70° C. without significantly impacting performance.

The invention also relates to a method of making the assembly comprising placing water and potassium bicarbonate in a first chamber of a package; mixing the DAM with PEG to form a DAM:PEG mixture; infusing the sponge with the DAM:PEG mixture to distribute DAM within the sponge and placing the sponge, DAM and PEG in a second chamber of the package. Infusing the sponge includes solubilizing the DAM:PEG mixture in a solvent with a low boiling point, such as ethanol, to form an ethanol-DAM-PEG solution and applying the ethanol-DAM-PEG solution evenly to the sponge.

The ethanol-DAM-PEG solution may be applied to the sponge in different ways such as dipping the sponge in the ethanol-DAM-PEG solution or brushing or spraying the ethanol-DAM-PEG solution on to the sponge or applying the ethanol-DAM-PEG solution with a syringe. Preferably the ethanol-DAM-PEG solution contains the ethanol and the DAM:PEG mixture at a ratio of 2.25 and the PEG has a molar mass of 200 g/mol (PEG 200). PEG with other g/mol molar masses are also effective. Preferably, the ethanol is anhydrous ethanol and is removed by applying heat and/or vacuum to the sponge. After the application of heat or vacuum, the next step is to verify that the ethanol has been removed and then to seal the second chamber.

The preceding summary is provided to facilitate an understanding of some of the innovative features unique to the present disclosure and is not intended to be a full description. A full appreciation of the disclosure can be gained by taking the entire specification, claims, drawings, and abstract as a whole.

BRIEF DESCRIPTION OF THE DRAWINGS

The disclosure may be more completely understood in consideration of the following description of various illustrative embodiments in connection with the accompanying drawings.

FIG. 1B is cross sectional view of the assembly of FIG. 1A.

FIG. 1C is a cross sectional view of the sponge removed from the package of FIG. 1A.

DESCRIPTION OF THE PREFERRED EMBODIMENTS

Figure 1A:
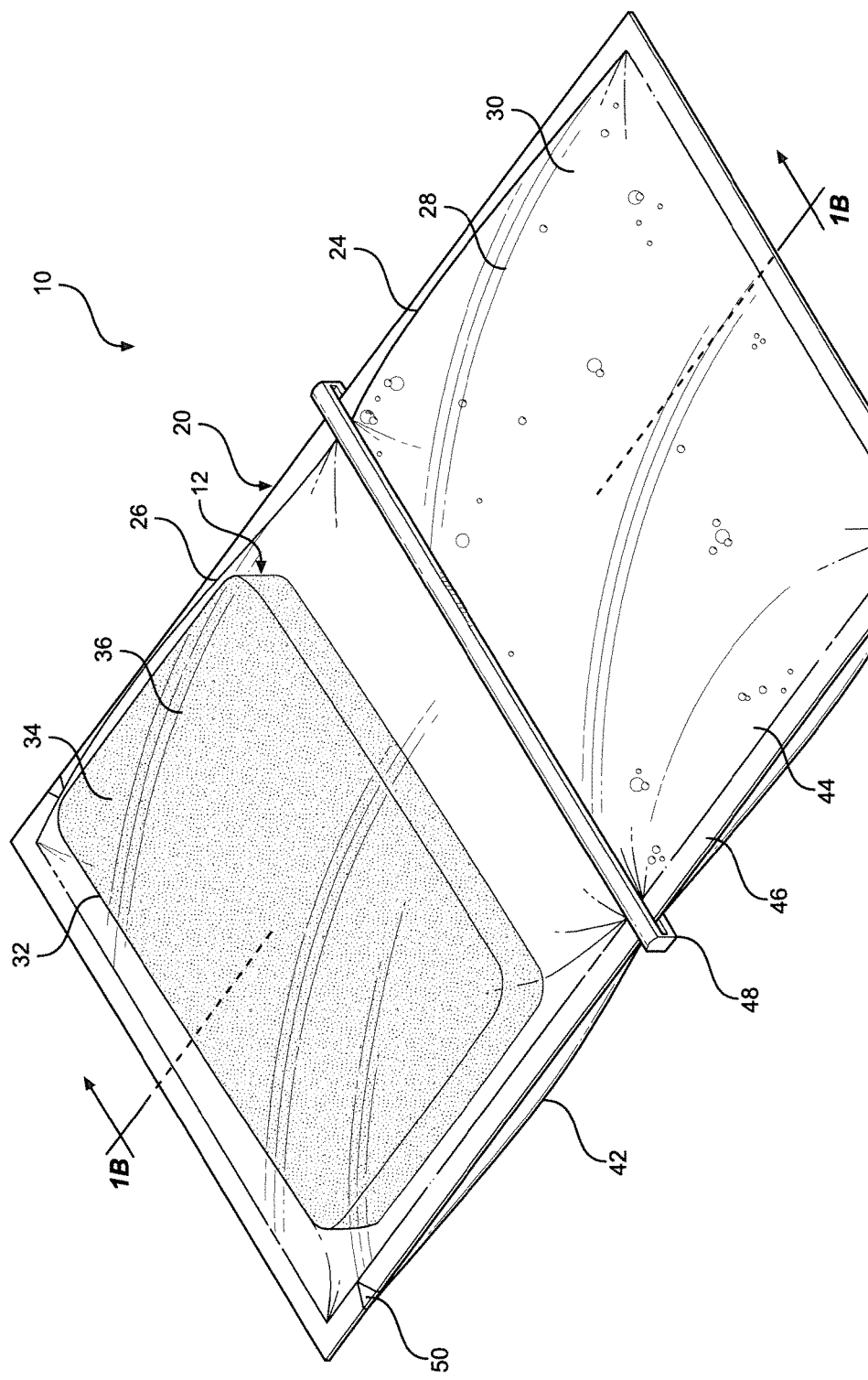
FIG. 1A is a perspective view of an assembly with a clear package with a physical barrier between the two chambers.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary. While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

As used in this specification and the appended claims, the singular forms "a", "an" and "the" include plural referents unless the content clearly dictates otherwise. As used in this specification and the appended claims, the term "or" is generally employed in its sense including "and/or" unless the content clearly dictates otherwise.

In the description of embodiments disclosed herein, any reference to direction or orientation is merely intended for convenience of description and is not intended in any way to limit the scope of the present invention. Relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise.

As used throughout, any ranges disclosed herein are used as shorthand for describing each and every value that is within the range. Any value within the range can be selected as the terminus of the range. All percentages are by weight unless otherwise indicated.

With reference to FIGS. 1A and 1B there is shown an assembly 10 containing a shelf-stable formulation 12 for decontaminating skin exposed to nerve agents. Assembly 10 includes a bi-pack package 20 forming a first chamber 24 and a second chamber 26. Water 28 and potassium bicarbonate 30 are located in first chamber 24. A sponge 32, polyethylene glycol (PEG) 34, and diacetylmonoxime (DAM) 36 are located in second chamber. In addition to PEG 34, package 20 may contain additional additives which will not react with DAM. For example, fragrances, moisturizers and surfactants may be added.

Package 20 is preferably formed with a bottom sheet 42 and a top sheet 44 that are connected at an outer periphery by a seal 46. A clamp 48 compresses bottom sheet 42 and top sheet 44 along a line extending across package 20 to form first chamber 24 and second chamber 26. Clamp 48 prevents water 28 and potassium bicarbonate 30 from entering second chamber 26 during storage and transport of package 20. Preferably, top sheet 44 is formed from clear plastic so that sponge 32 and water can be seen there through. Clamp 48 is preferably configured to be easily broken or removed to allow water 28 and potassium bicarbonate 30 to enter second chamber 26. Cutouts 50 are provided in both top and bottom sheets 44, 42 in seal 46 so as to allow package 20 to be easily torn open by a user to access sponge 32 so that sponge 32 may be removed. Clear plastic allows for a user to clearly see the progression of water 28 and potassium bicarbonate 30 into sponge 32 so the user can keep shaking package 20 until sponge 32 is completely wet before tearing cutouts 50.

Potassium bicarbonate 30 is present in water 28 as a solution. DAM 36 and PEG 34 are distributed uniformly throughout sponge 32 and are relatively dry. DAM 36 is an active ingredient and comprises 2, 3, butanedione monoxime, which is also referred to as diacetyl monoxime. Derivatives of DAM 36 may also be used wherein the alkyl group includes four to six carbon atoms. DAM 36 and its derivatives will react with targeted toxic compounds such as chemical/nerve agents to cause the toxic compounds to decompose into non-toxic components. DAM 36 is also effective against toxic industrial chemicals, and acids. More details about DAM and its derivatives are discussed in U.S. Pat. No. 9,604,085, incorporated herein by reference.

In use, assembly 10 may be stored for relatively long periods of time. Package 20 is carried by military personnel or first responders. When skin is exposed to a chemical nerve agent, clamp 48 is removed and package 20 is shaken to move water 28 and potassium bicarbonate 30 into sponge 32. Once sponge 32 is wet, package 20 is torn open at cutouts 50. Sponge 32 is then removed and wiped on the exposed skin to spread DAM 36 over the affected area to neutralize the nerve agent. PEG 34 acts as a carrier to aid in applying DAM 36 to skin. Preferably, PEG 34 has a molar weight of 200 although other molar weights are acceptable. DAM 36 is applied by scrubbing the exposed area with sponge 32. DAM 36 and PEG 34 are preferably allowed to stay on the affected area of skin for several minutes before removal. DAM 36 and PEG 34 are then reapplied.

A preferred composition of the ingredients, by weight percent, in each chamber of the assembly is as follows:
Chamber 1
Water 78.3% 14.4 (g)
Potassium Bicarbonate 21.7% 4.0 (g)
Chamber 2
DAM 58.5% 3.61 (g)
PEG 22.5% 1.39 (g)
Ethanol 19.0% 1.17 (g)
Sponge –% 1.54 (g)

The above formulations were developed for chambers 24, 26 of assembly 10. The ingredients can be varied up or down by ten percent. Potassium bicarbonate can be removed entirely leaving only water in first chamber 24. The water can range from about 70% to about 100% and is preferably present from 76% to about 80% and, most preferably 78.3%. The potassium bicarbonate is present from about 0% to 30% and more preferably, 24% to 20% and, most preferably, 21.7%. Other inert ingredients may be present in first chamber 24. Preferably substantially all of the ethanol is removed in processing and may vary between 0 and 20%. The ratio of DAM to PEG should be 2.25 and maintained within the 10% variation. Ethanol is included in the formulation to solubilize the DAM and PEG. Once infused into the sponge, the ethanol is removed via vacuum and is not present in Chamber 2, as discussed in more detail below. While ethanol is described, other low boiling point solvents may be employed.

Figure 2A:
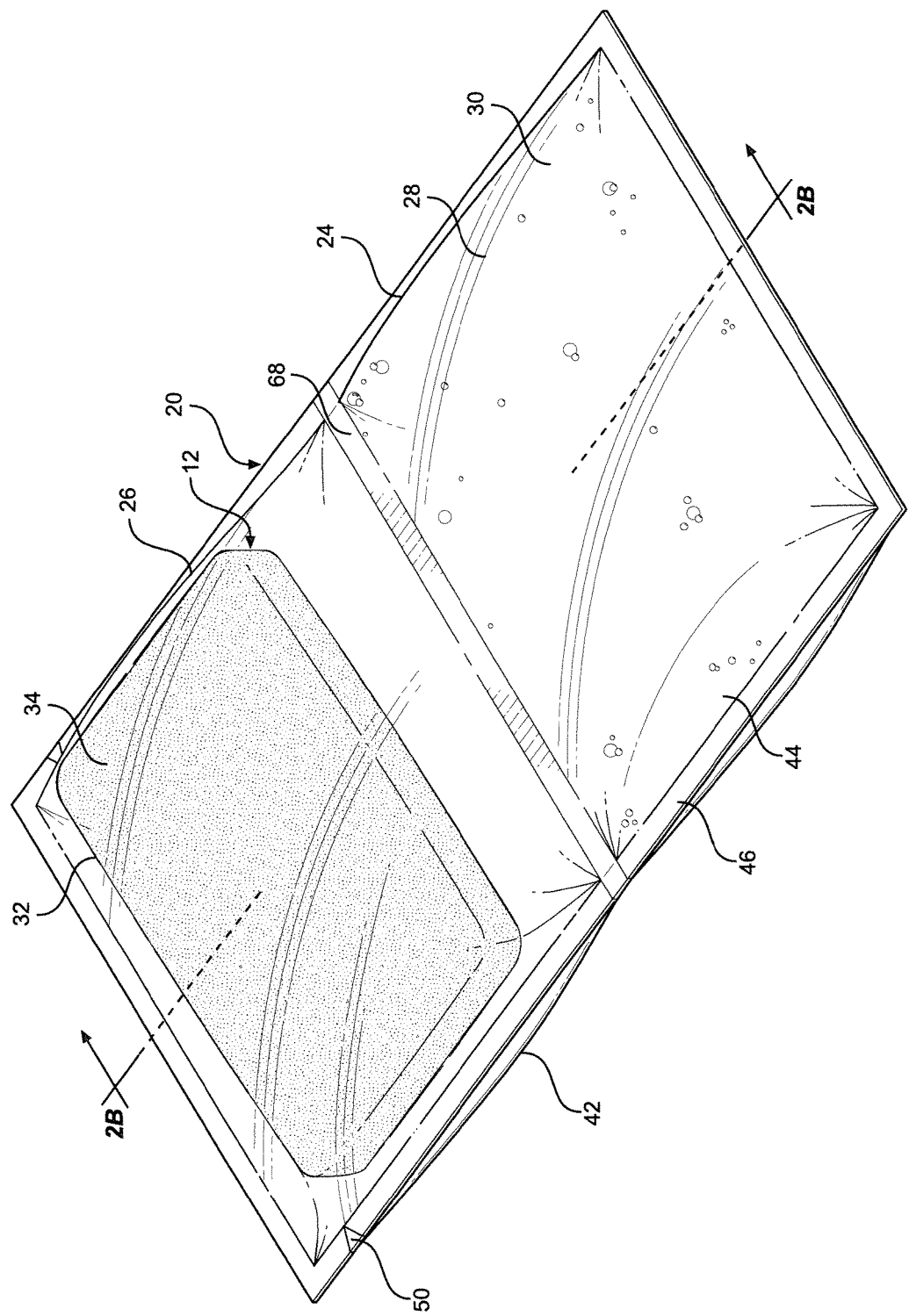
FIG. 2A is a perspective view of an assembly with a clear package with a thermal seal between the two chambers.
Figure 2B:
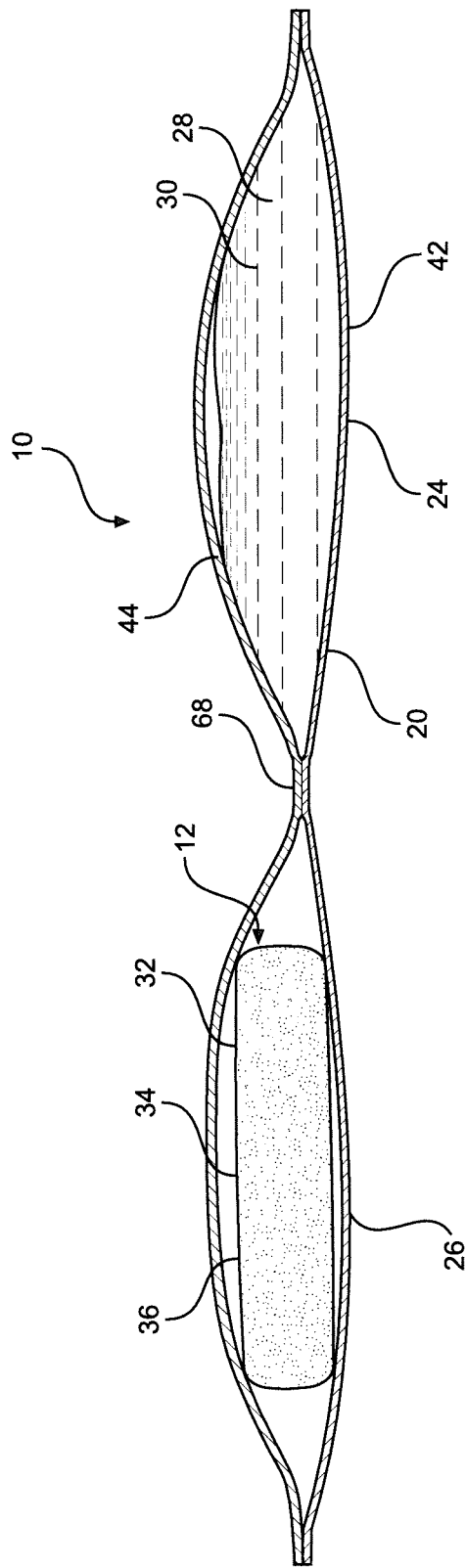
FIG. 2B is cross sectional view of the assembly of FIG. 2A.
Figure 3:
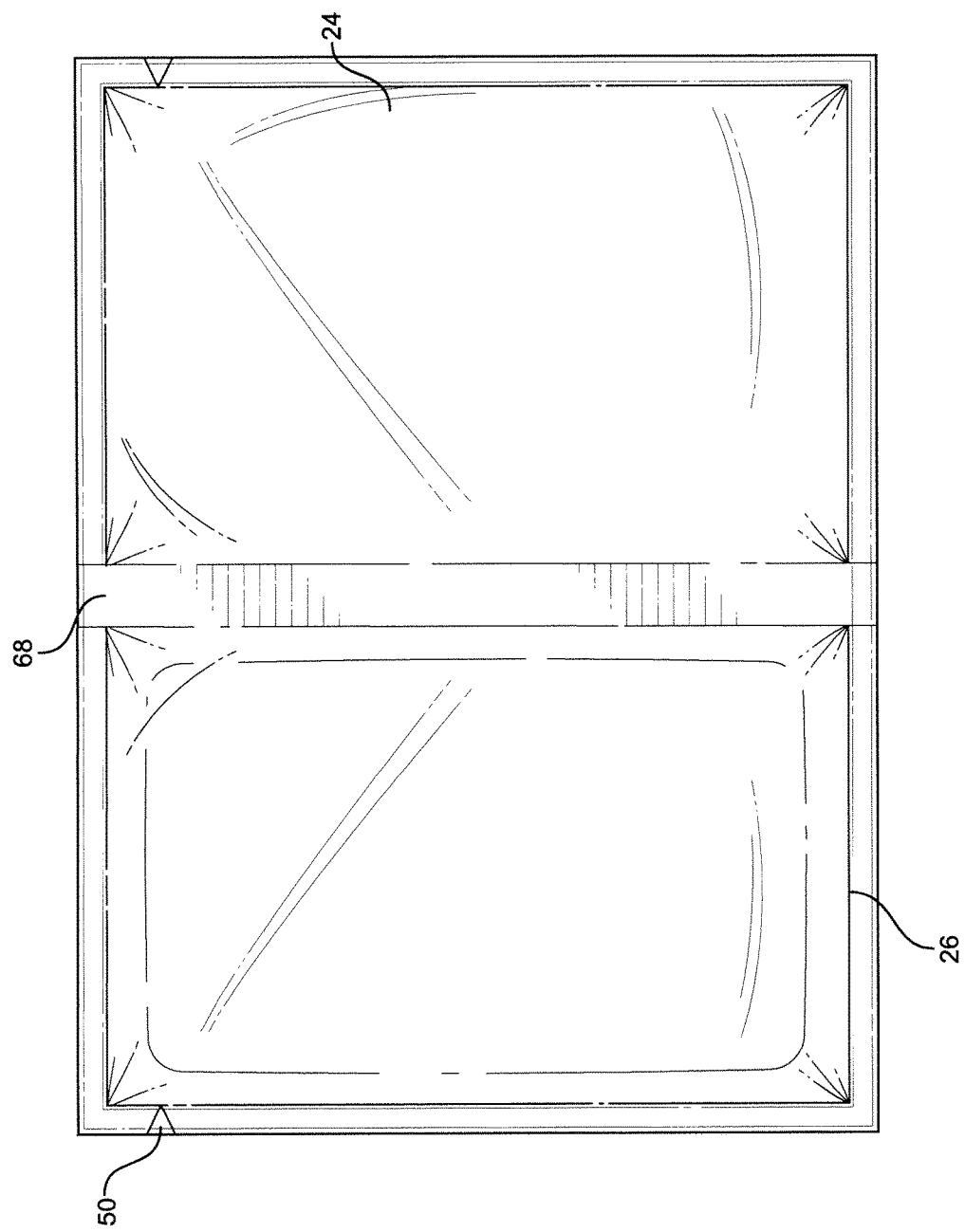
FIG. 3 is a top view of an assembly with a metalized package with a thermal seal between two chambers.
Figure 4:
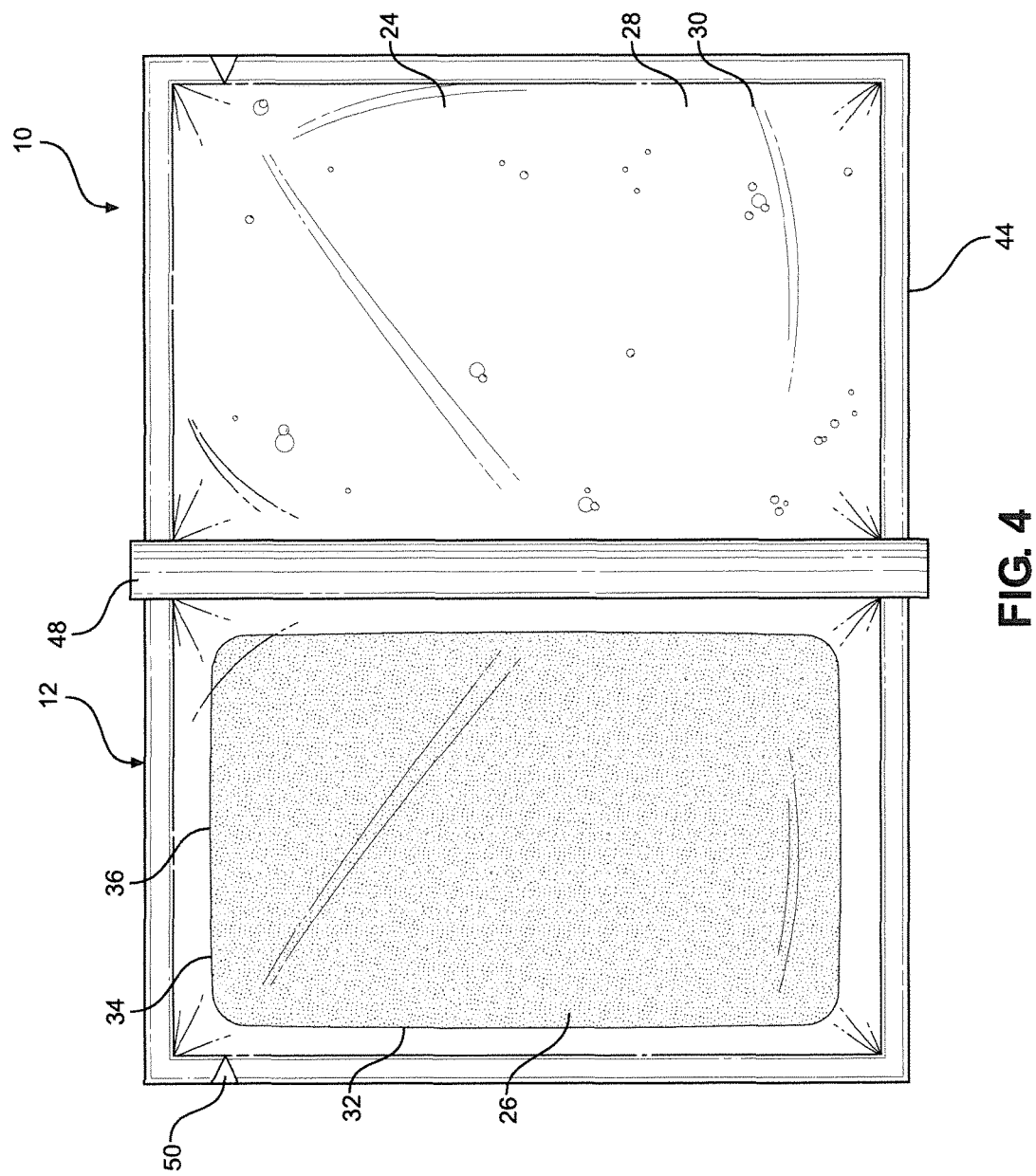
FIG. 4 is a top view of an assembly with a clear package with a physical barrier between two chambers.

As best seen in FIGS. 2A, 2B and 3, another embodiment of the invention is shown wherein clamp 48 has been replaced by a thermal seal 68. Thermal seal 68 separates first chamber 24 from second chamber 26 in a similar manner to clamp 48. Thermal seal 68 has an advantage over clamp 48 since it cannot be dislodged during transport of package 20 while clamp 48 can be easily removed when compared to thermal seal 68. When assembly 10 is to be used, thermal seal 68 is broken to allow water 28 to enter second chamber 26, and then package 20 is shaken before being torn open at cutouts 50. Turning now to FIG. 4 there is shown another embodiment of the invention, wherein top and bottom sheets are made of a metallized material. The metallized material serves to protect the DAM 36 and PEG 34 and extend shelf life of package 20. It should be noted that the potassium bicarbonate is optional and therefore is not shown in this embodiment such that only water is in the first chamber.

Several experiments and investigations were conducted to show the effectiveness of the preferred embodiments. The prior art arrangement using RSDL was shown to have a projected shelf life of 4 years at 30° C. and that short term excursions above that temperature range can substantially degrade the active material. DAM was aged under a variety of conditions. DAM was tested neat (as standalone component) at 30° C., 50° C. and 70° C. DAM neat is a stable compound and showed little propensity to age after 6-7 weeks at 70° C. DAM was also tested with PEG 200 again at 30° C., 50° C. and 70° C. Some changes were seen at high temperatures 70° C. after two weeks. Next DAM was tested in water again at 30° C., 50° C. and 70° C. DAM in the presence of water rapidly aged after 1 week at 70° C. Aging was monitored using 1H nuclear magnetic resonance (NMR) spectra. This aging was retarded somewhat by the presence of potassium bicarbonate. The results for DAM with PEG 200 is intermediate those of DAM neat and DAM with water and potassium bicarbonate and showed some changes at high temperatures (70° C.) after 2 weeks.

Figure 5A:
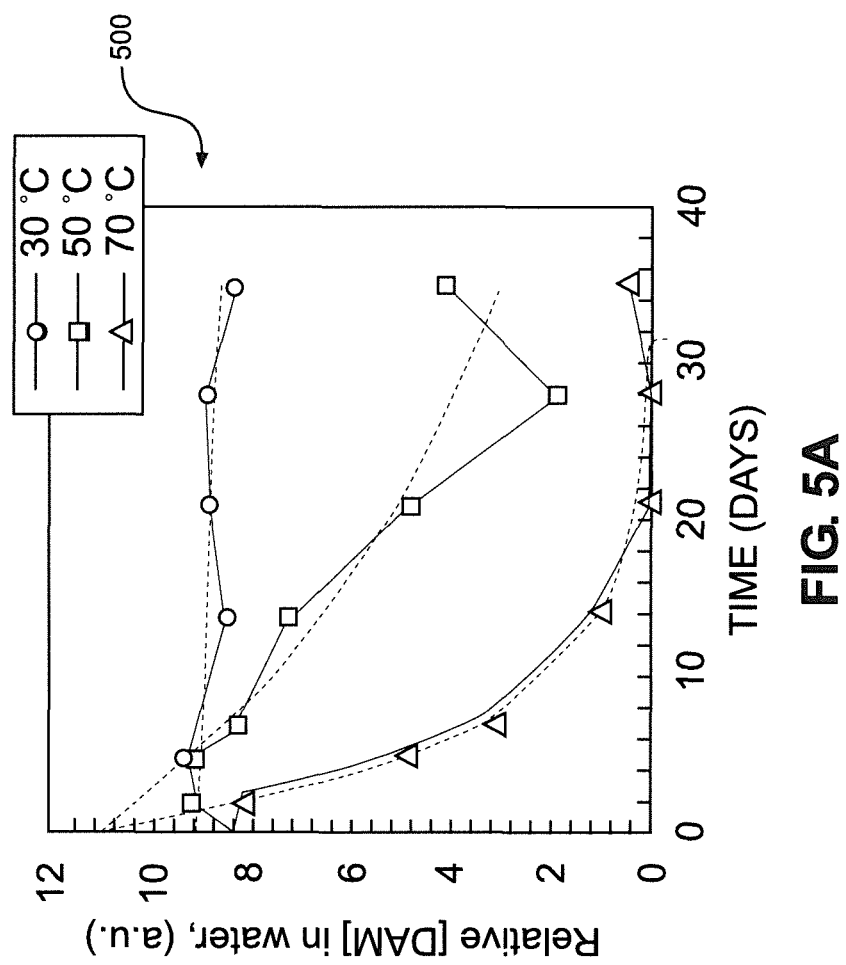
FIGS. 5A-5C are graphs showing the reaction kinetics of DAM in water.
Figure 5B:
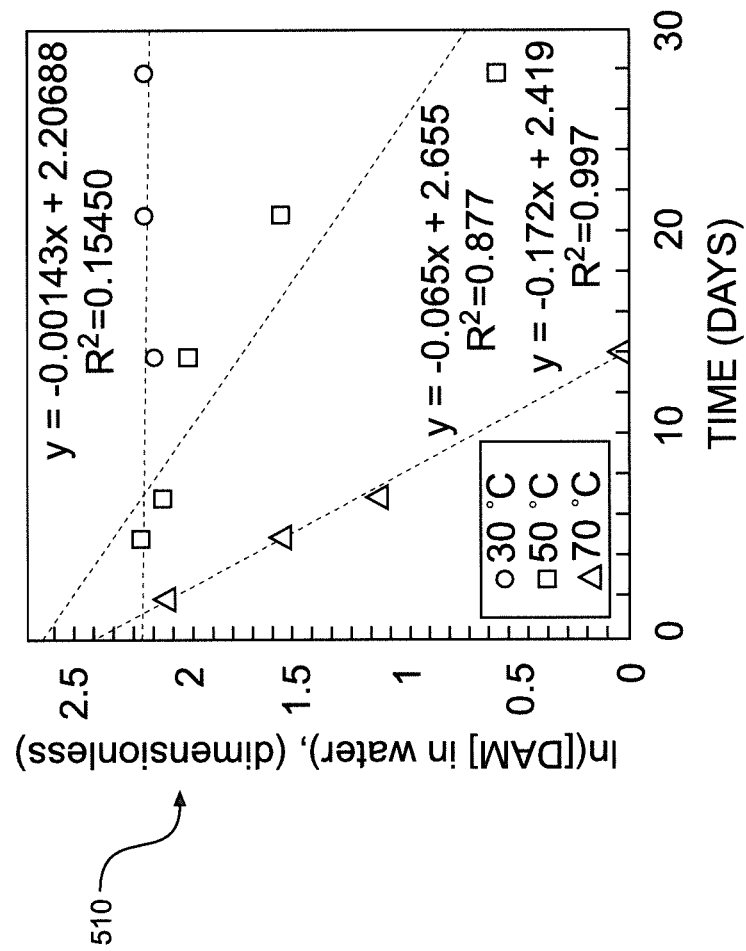
Figure 5C:
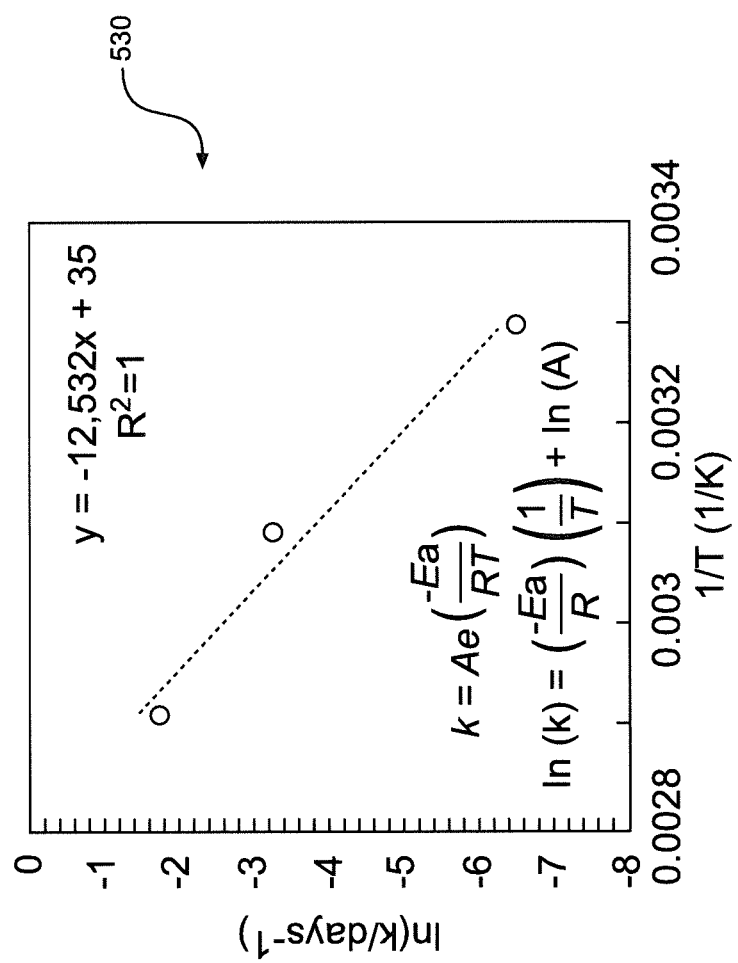

The rate kinetics of DAM degradation into dimethylglyoxime (DMG) were then studied. First, an empirical rate law with a mass action kinematics model was developed for DAM aging in water. The empirical data is shown in graph 500 in FIG. 5A. Specifically, graph 500 includes data showing how measured DAM concentration in water changes over time. The empirical data fits a first order mass action reaction kinetics model as shown in graph 510 in FIG. 5B. Based on DAM's postulated degradation mechanism, the model is likely pseudo first order and largely dependent on the hydrolysis step, since water is present in excess and the concentration of water can be considered constant. Rate constants were derived from the linearized $1^{st}$ order reaction model shown in FIG. 5B and used to derive an Arrhenius Thermal model 530 (for reaction constant versus temperature) as shown in FIG. 5C.

$$E\_a = -slope * R = 12,532 * 8.314 = 104 \text{ kJ/mol}$$

$$A = e^\wedge \text{intercept} = e^\wedge 35 = 1.611 \times [10]^\wedge 15 [\text{days}]^\wedge(-1)$$

The parameters from the Arrhenius model were used to predict the rate constant and half-life at room temperature for DAM in water at various storage temperatures. See table 1. At 20° C. the half-life is >4 years, which is consistent with the stated product shelf life.

TABLE 1

| Temperature | 20° C. | 30° C. | 50° C. | 70° C. |
|---|---|---|---|---|
| k (days$^{-1}$) = | 0.000447 | 0.00143 | 0.0374 | 0.172 |
| $t_{1/2}$ (days) = | 1585 | 485 | 18.5 | 4.03 |
| $t_{1/2}$ (years) = | 4.34 | 1.33 | 0.0507 | 0.0111 |

Figure 6A:
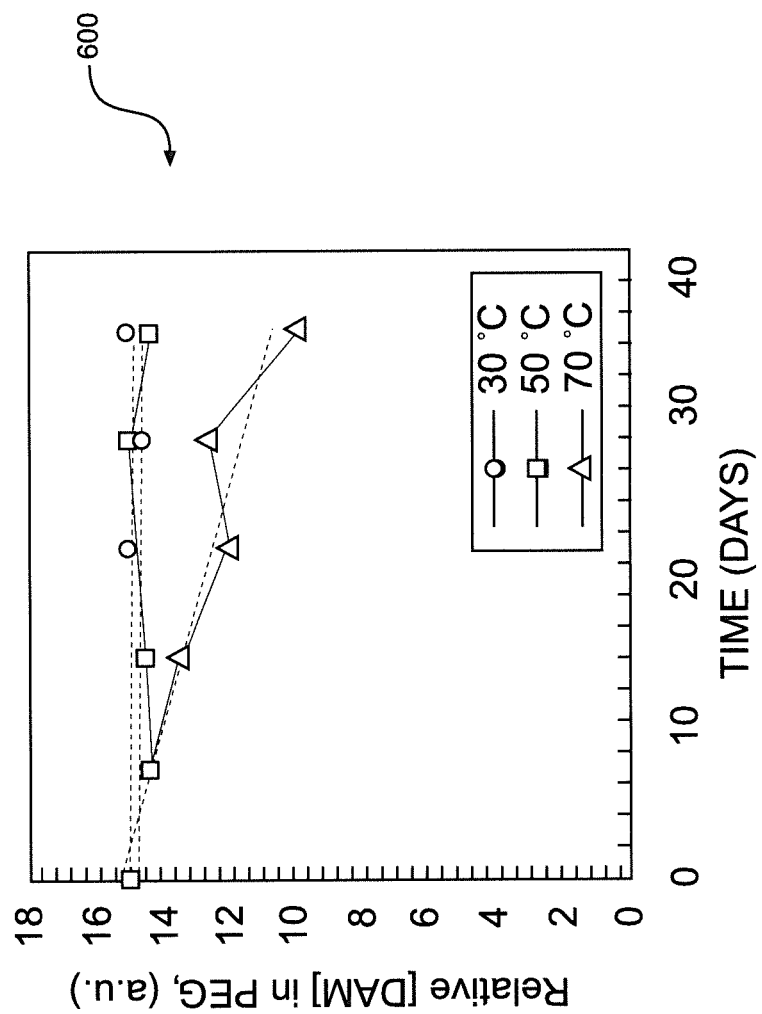
FIGS. 6A-6C are graphs showing the reaction kinetics of DAM in PEG200.
Figure 6B:
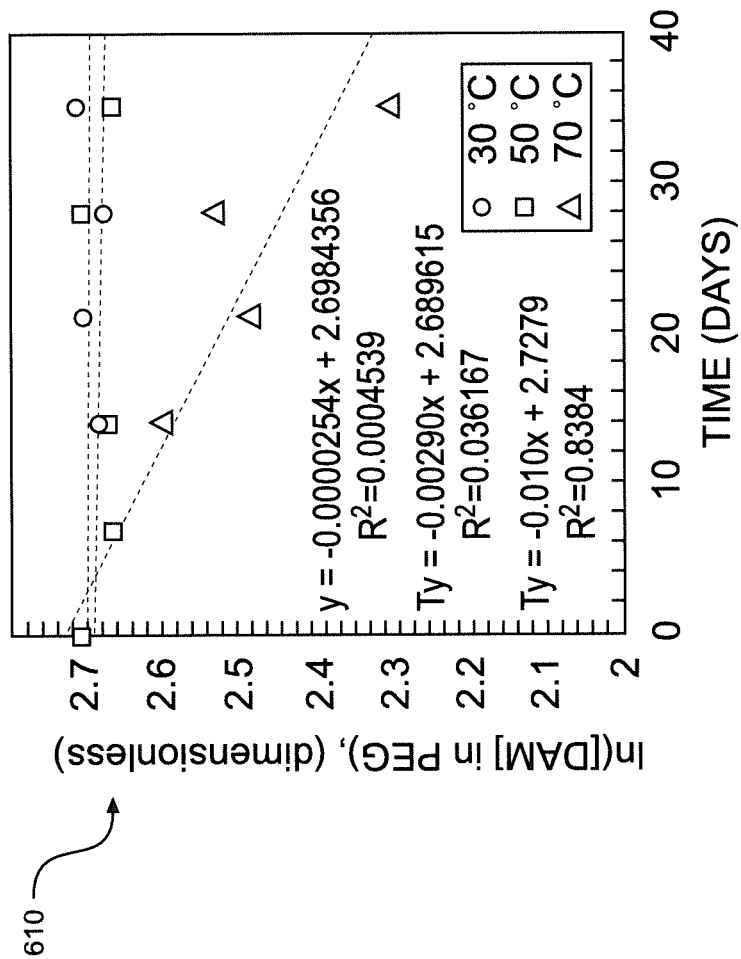
Figure 6C:
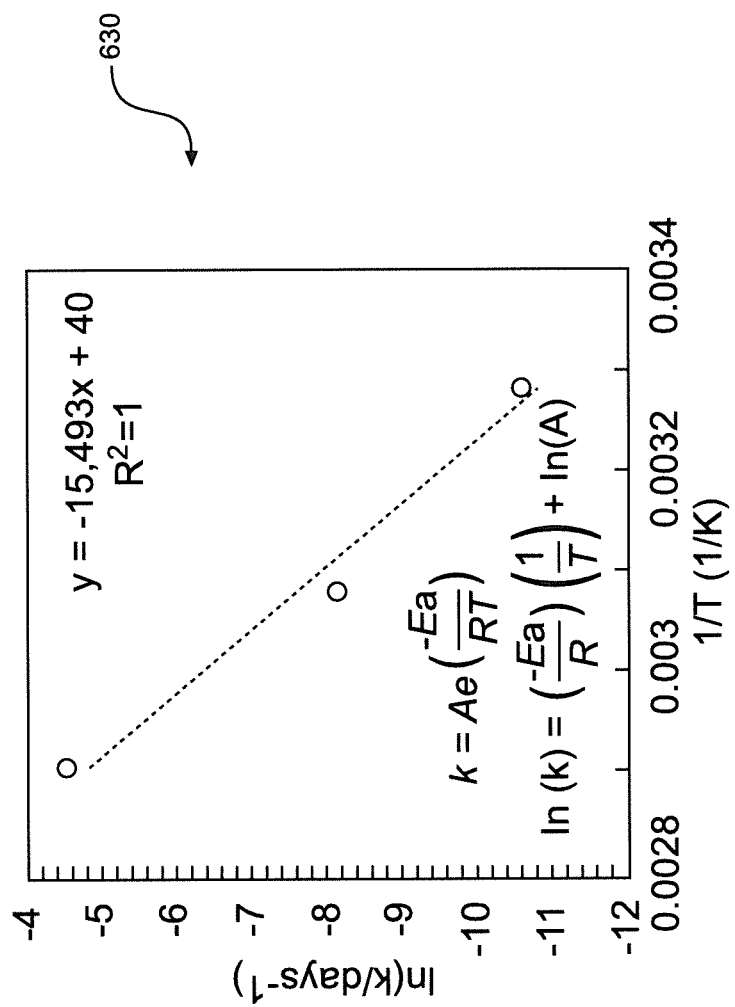

An empirical rate law with a mass action kinematics model was then produced for DAM in PEG 200. The empirical data is shown in graph 600 in FIG. 6A. Specifically, graph 600 includes data showing how measured DAM concentration in PEG 200 changes over time. The empirical data fits a first order reaction model as shown in graph 610 of FIG. 6B. Rate constants were derived from the linearized $1^{st}$ order reaction model shown in FIG. 6B and used to derive an Arrhenius Thermal model 630 (for reaction constant versus temperature) as shown in FIG. 6C.

$$E\_a = -slope * R = 12,532 * 8.314 = 129 \text{ kJ/mol}$$

$$A = e^\wedge \text{intercept} = e^\wedge 35 = 3.157 \times [10]^\wedge 17 [\text{days}]^\wedge(-1)$$

The parameters from the Arrhenius model were used to predict the rate constant and half-life at room temperature of DAM in PEG 200 at various storage temperatures. See table 2. At 20° C. the half-life is >539 years, which constitutes an expectedly long time.

TABLE 2

| Temperature | 20° C. | 30° C. | 50° C. | 70° C. |
|---|---|---|---|---|
| k (days$^{-1}$) = | 3.52E−06 | 2.54E−05 | 0.000290 | 0.0101 |
| $t_{1/2}$ (days) = | 196700 | 27255 | 2392 | 68.4 |
| $t_{1/2}$ (years) = | 539 | 74.7 | 6.55 | 0.187 |

Figure 7:
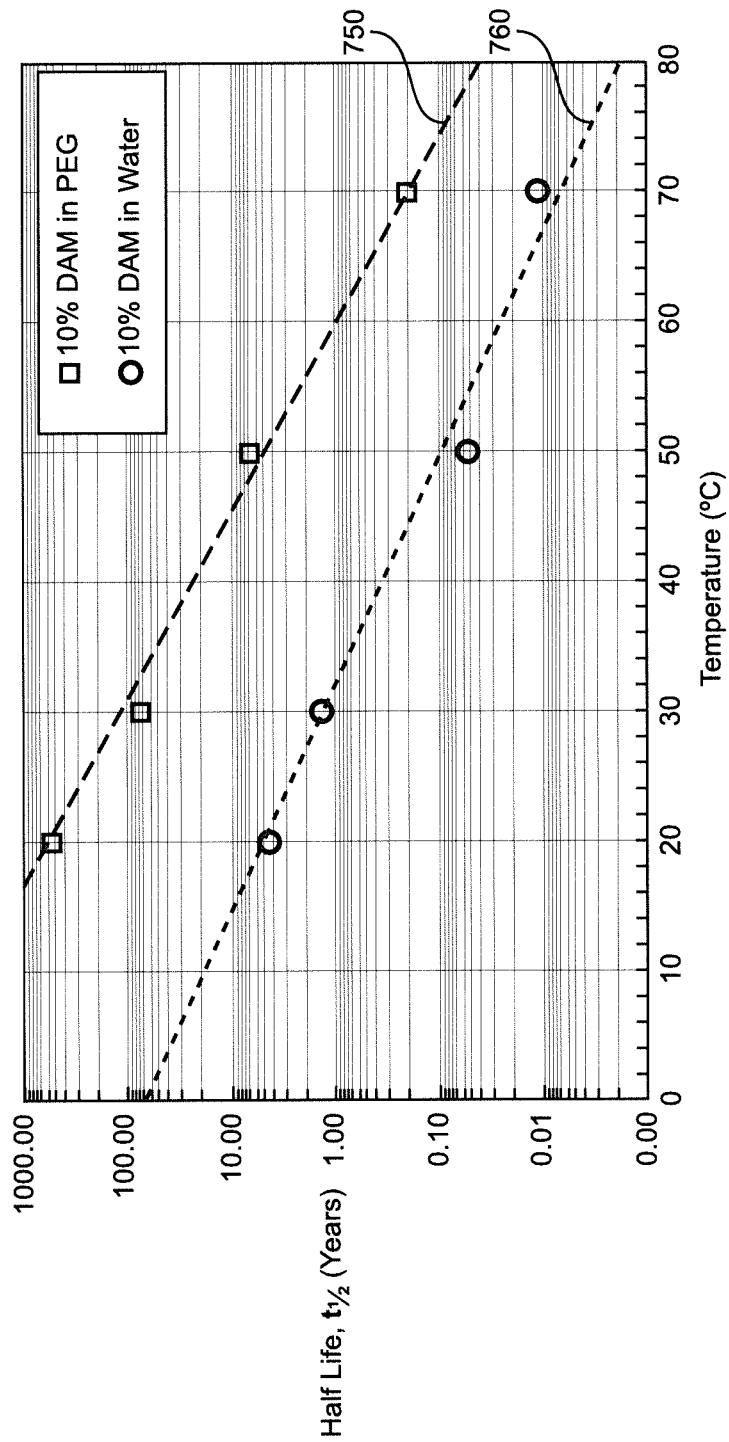
FIG. 7 is a graph showing half-life projections of the amount of DAM over time using the Arrhenius model parameters.

FIG. 7 shows Half-life projections for 10% DAM in PEG (plot 750) and for 10% DAM in water (plot 760) and indicates that separating the DAM component from water substantially improves the degradation kinetics of the decontaminating formulation. DAM stored with PEG has a projected room temperature half-life of hundreds of years. DAM stored in water has a projected room temperature half-life of 2.5 years. The temperature corresponding to a 4-year shelf life increases from 20° C. to 50° C. when the water and DAM are separated. At 70° C., the shelf life is increased by an order of magnitude (factor of 17), from 4 days to 68 days. This will allow short term excursions to higher temperatures to be experienced by the product more often with minimal impact.

Figure 8:
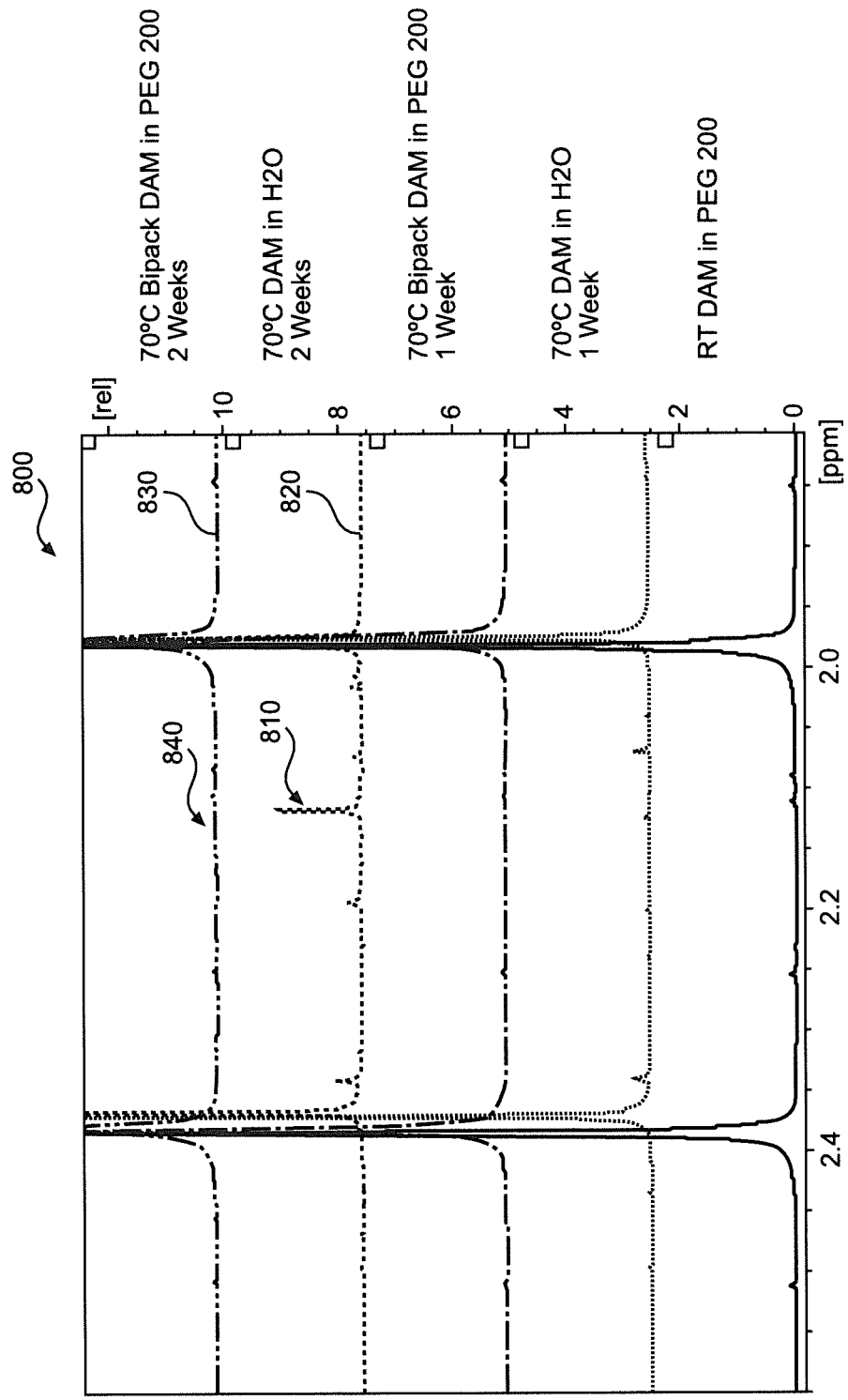
FIG. 8 is a series of NMR spectra showing the chemical effects of aging the DAM in a Bi-Pack over time.
Figure 9:
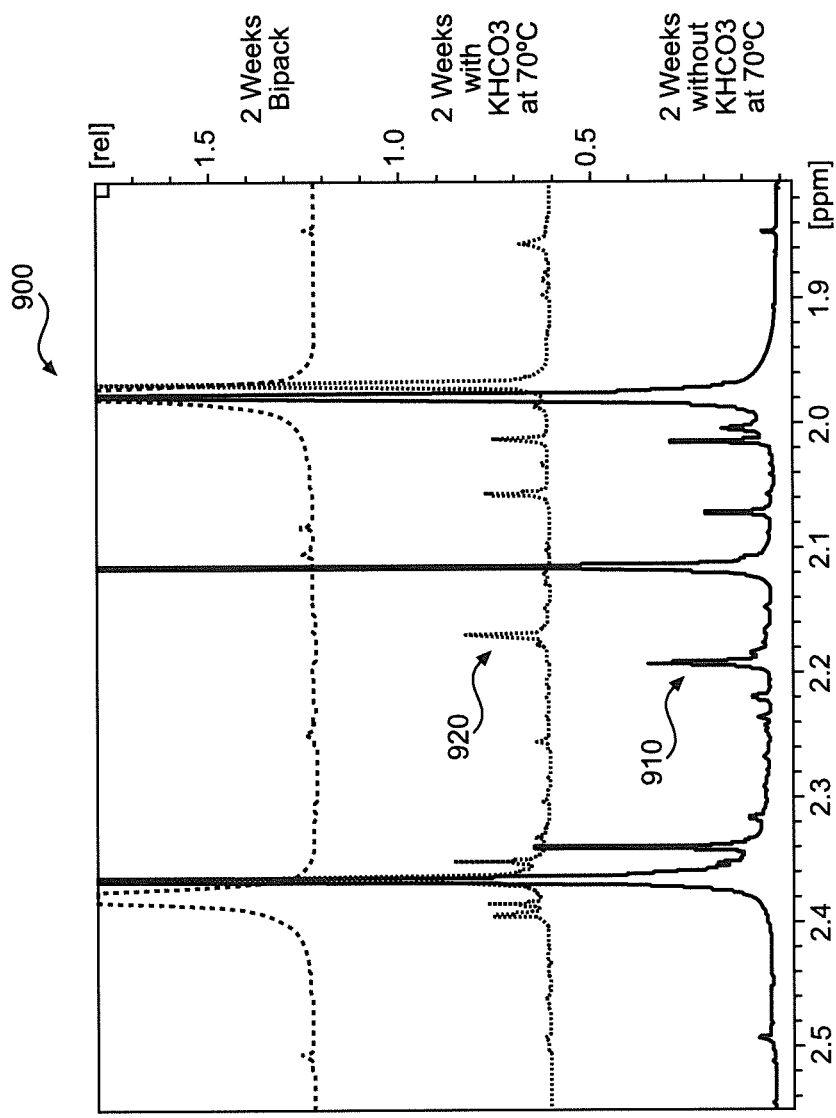
FIG. 9 is a series of NMR spectra showing the chemical effects of aging the DAM with potassium bicarbonate in a Bi-Pack over time.

FIG. 8 is an NMR spectra 800 showing the degradation of DAM when placed in a bi-pack package 20. Degradation of DAM into degradation products shows as peak 810 in the curve 820 as early as 2 weeks with DAM in water but no degradation is present in the bipack with DAM in PEG curve 830 as shown by the lack of peaks at 840. FIG. 9 is an NMR spectra 900 showing the impact of adding potassium bicarbonate. The degradation without Potassium Bicarbonate, as shown by peaks 910, is more than with Potassium Bicarbonate as shown by peaks 920.

Figure 10A:
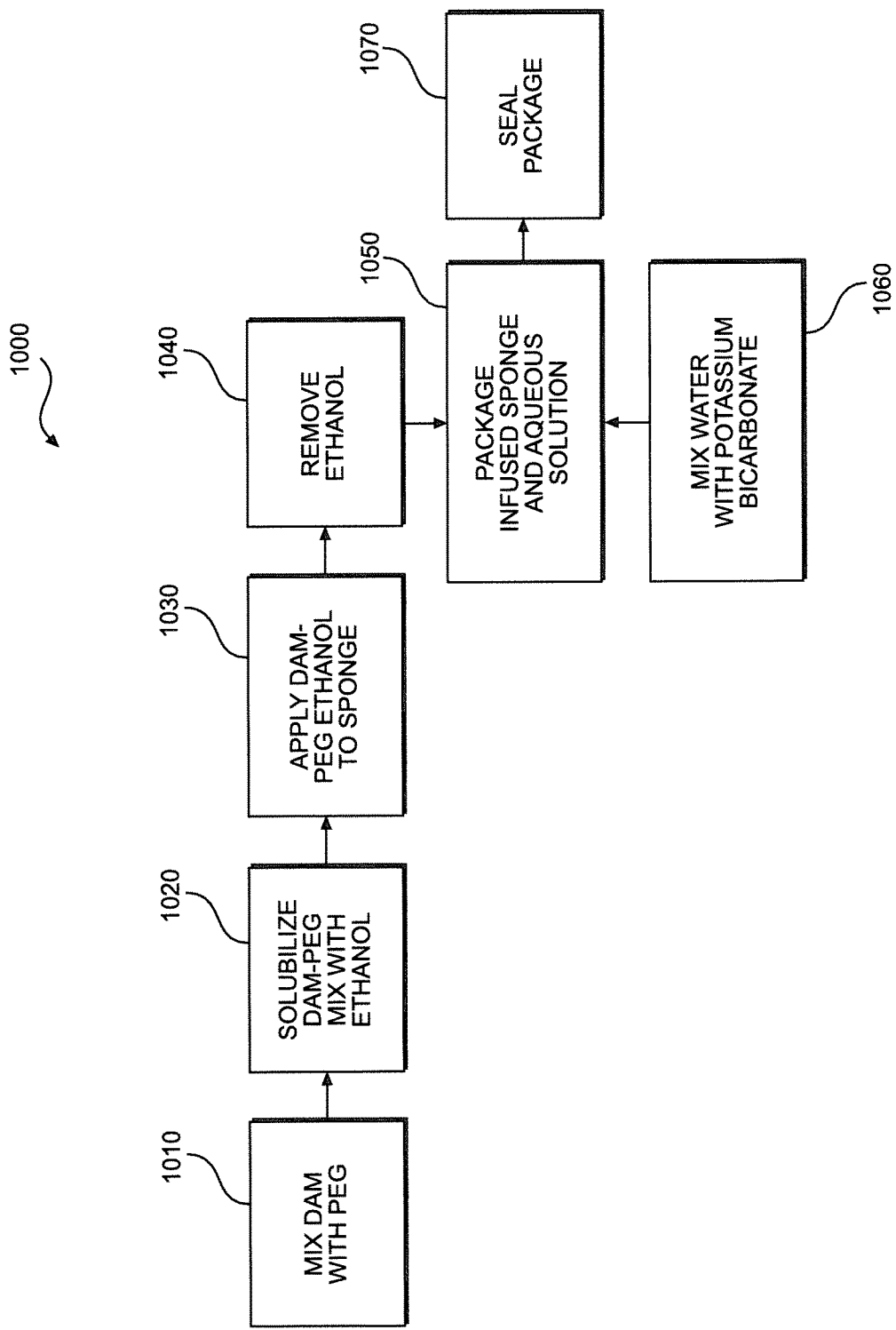
FIG. 10A is a flow chart showing a method of manufacturing the package and contents of the assembly shown in FIG. 1.

As shown in FIGS. 1 and 10A, assembly 10 is made in the following manner, as shown in chart 1000. First DAM 36 is mixed, at 1010, with PEG 34 to form a thick mixture. Ethanol or another low boiling point solvent is used to solubilize DAM 36 and PEG 34 at 1020 which is then applied to sponge 32 at 1030. Ethanol is removed by heat or vacuum at the time of preparation at 1040. Sponge is placed in first chamber 24 of package at 1050. Water and potassium bicarbonate are mixed at 1060 and placed in second chamber 26 of package, at 1050. Package 20 is then sealed at 1070 with a heat sealer.

Figure 10B:
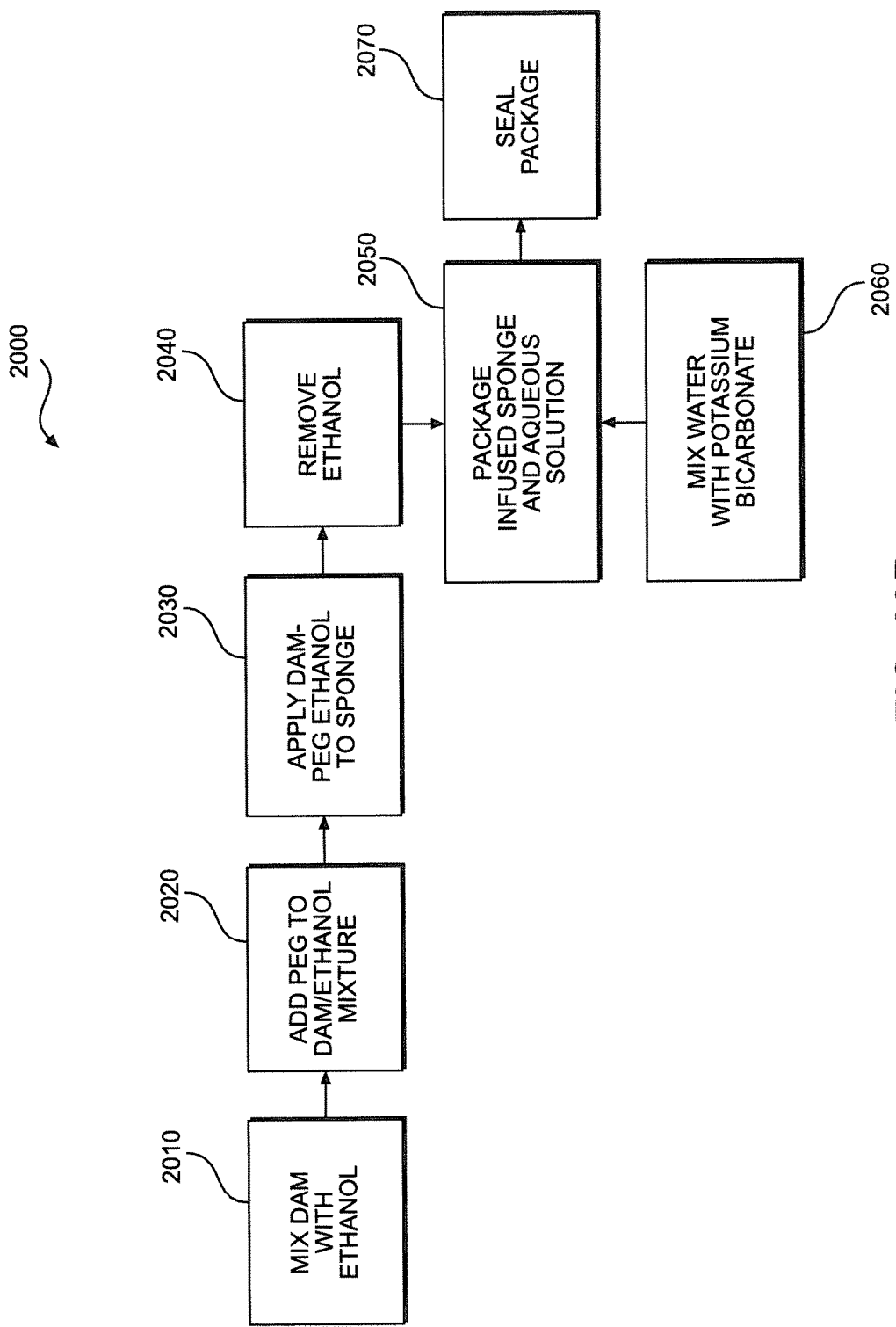
FIG. 10B is a flow chart showing an alternative method of manufacturing the package and contents of the assembly shown in FIG. 1.

In alternative embodiment shown in FIG. 10B, assembly 10 is made as shown in chart 2000. First DAM is mixed with ethanol or another low boiling point solvent, at 2010. Then, at 2020 PEG is added to form a DAM-PEG-Solvent(Ethanol) mixture that is applied to sponge 32 at 2030. Ethanol is removed by heat or vacuum at the time of preparation at 2040. Sponge is placed in first chamber 24 of package at 2050. Water and potassium bicarbonate are mixed at 2060 and placed in second chamber 26 of package, at 2050. Package 20 is then sealed at 2070 with a heat sealer.

Figure 10C:
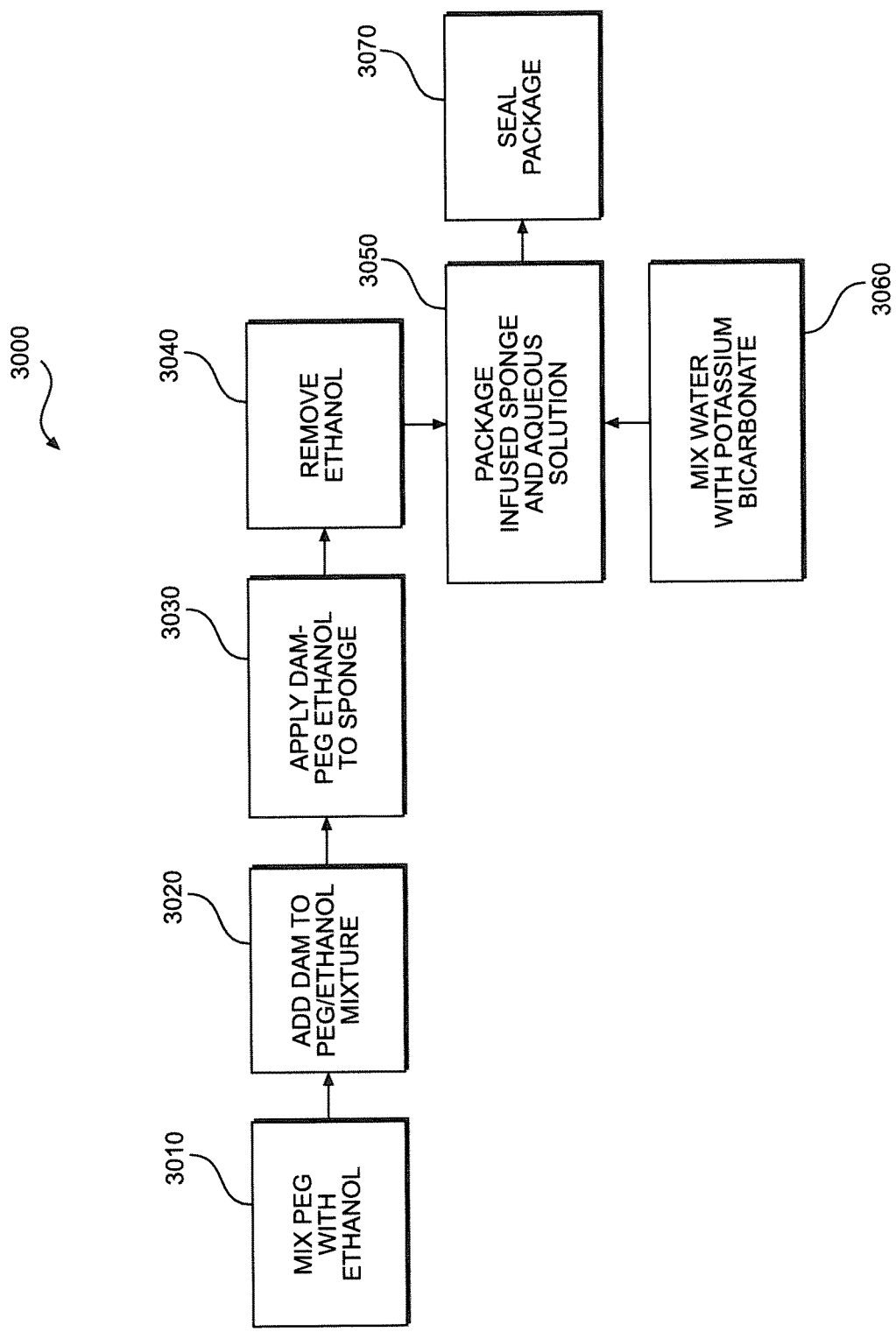
FIG. 10C is a flow chart showing yet another alternative method of manufacturing the package and contents of the assembly shown in FIG. 1.

In alternative embodiment shown in FIG. 10C, assembly 10 is made as shown in chart 3000. First PEG is mixed with ethanol or another low boiling point solvent, at 3010. Then, at 3020 DAM is added to form a DAM-PEG-Solvent (Ethanol) mixture that is applied to sponge 32 at 3030. Ethanol is removed by heat or vacuum at the time of preparation at 3040. Sponge is placed in first chamber 24 of package at 3050. Water and potassium bicarbonate are mixed at 3060 and placed in second chamber 26 of package, at 3050. Package 20 is then sealed at 3070 with a heat sealer. The DAM, PEG and solvent could also be mixed in any order, in one step or multiple steps, so long as a DAM-PEG-Solvent(Ethanol) mixture is produced.

It should be noted that if DAM and PEG are mixed with water the resulting solution can easily be infused into a sponge. Surprisingly, if DAM and PEG are mixed without water, a relatively thick mixture is formed. The mixture is difficult to work with and cannot be easily supplied to a sponge. If DAM and PEG are mixed with a low boiling point solvent such as ethanol, surprisingly the resulting solution is easily infused into a sponge and the ethanol can be removed without damaging the sponge, DAM or PEG resulting in a relatively dry sponge infused with DAM and PEG that has a long shelf life. The DAM and PEG are preferably diffused throughout sponge 32. However, the DAM and PEG need only achieve 5%-50% penetration into sponge 32 to still be effective. The addition of potassium bicarbonate is optional and mixing in water only at steps 1060 and 2060 represent a further preferred embodiment of the invention. The resulting assembly meets the needs in the art of having a device that can be used to counter the effects of chemical warfare nerve agents even after being stored for years.

Having thus described several illustrative embodiments of the present disclosure, those of skill in the art will readily appreciate that yet other embodiments may be made and used within the scope of the claims hereto attached. Numerous advantages of the disclosure covered by this document have been set forth in the foregoing description. It will be understood, however, that this disclosure is, in many respect, only illustrative. Changes may be made in details, particularly in matters of shape, size, and arrangement of parts without exceeding the scope of the disclosure. The disclosure's scope is, of course, defined in the language in which the appended claims are expressed.

What is claimed is:

1. An assembly containing a shelf-stable formulation for decontaminating skin exposed to toxic compounds comprising:
    a package forming a first chamber and a second chamber;
    water located in the first chamber; and
    a dry sponge and diacetylmonoxime or derivatives thereof, located in the second chamber, wherein the diacetylmonoxime is distributed within the sponge.

2. The assembly of claim 1, further comprising potassium bicarbonate in the water and polyethylene glycol distributed within the sponge.

3. The assembly of claim 1, wherein the package is formed of transparent material.

4. The assembly of claim 1, wherein the package is formed of a metallized material.

5. The assembly of claim 1, wherein package further comprises a barrier between the first chamber and second chamber that is configured to be rapidly removed to enable the water to contact the sponge.

6. The assembly of claim 5, wherein the package is made of plastic and the barrier is a thermoformed seal and the package is configured to be torn open to allow for removal of the sponge.

7. The assembly of claim 1, wherein a ratio of potassium bicarbonate to water by weight is less than 1 to 3.6.

8. The assembly of claim 1, wherein a ratio of diacetylmonoxime to polyethylene glycol to by weight ranges from about 2.25 to about 2.59.

9. The assembly of claim 1, wherein the package has a shelf life of at least 5 years at 50° C.

10. A method of making an assembly containing a shelf-stable formulation for decontaminating skin exposed to toxic compounds, the method comprising:
    placing water in a first chamber of a package; and
    placing a sponge and diacetylmonoxime or derivatives thereof in a second chamber of the package.

11. The method of claim 10, further comprising:
    mixing the diacetylmonoxime with polyethylene glycol to form a diacetylmonoxime-polyethylene glycol mixture and then adding a solvent to form a solvent-diacetylmonoxime-polyethylene-glycol solution; and
    infusing the sponge with the solvent-diacetylmonoxime-polyethylene glycol solution to distribute diacetylmonoxime within the sponge.

12. The method of claim 10, further comprising:
mixing the diacetylmonoxime or the polyethylene-glycol with a solvent and then adding the diacetylmonoxime or the polyethylene-glycol to form a solvent-diacetyl-monoxime-polyethylene-glycol solution; and
infusing the sponge with the solvent-diacetylmonoxime-polyethylene glycol solution to distribute diacetylmonoxime within the sponge.

13. The method of claim 10, further comprising:
mixing the diacetylmonoxime with the polyethylene glycol and a solvent in any order to form a solvent-diacetylmonoxime-polyethylene-glycol solution; and
infusing the sponge with the solvent-diacetylmonoxime-polyethylene glycol solution to distribute diacetylmonoxime within the sponge.

14. The method of claim 13, wherein applying the solvent-diacetylmonoxime-polyethylene glycol solution to the sponge includes dipping the sponge in the solvent-diacetyl-monoxime-polyethylene glycol solution to distribute the solvent-diacetylmonoxime-polyethylene glycol solution throughout the sponge.

15. The method of claim 13, wherein applying the solvent-diacetylmonoxime-polyethylene glycol solution to the sponge includes brushing or spraying the solvent-diacetyl-monoxime-polyethylene glycol solution on to the sponge.

16. The method of claim 13, wherein applying the solvent-diacetylmonoxime-polyethylene glycol solution to the sponge is conducted with a syringe or by industrial liquid dosaging.

17. The method of claim 11, wherein the solvent is ethanol, the solvent-diacetylmonoxime-polyethylene glycol solution contains ethanol and the diacetylmonoxime-polyethylene glycol mixture at a ratio of about 2.25 and the polyethylene glycol has a molar mass of 200 g/mol.

18. The method of claim 17, wherein the ethanol is anhydrous ethanol and further comprising removing the anhydrous ethanol by applying heat and/or vacuum to the sponge and adding potassium bicarbonate to the water in the first chamber.

19. The method of claim 18 further comprising verifying that the ethanol has been removed.

20. The method of claim 10 further comprising sealing the first chamber from the second chamber with a heat sealer.

* * * * *